United States Patent [19]
McFadden

[11] Patent Number: 5,560,728
[45] Date of Patent: Oct. 1, 1996

[54] POSITIONING DEVICE ADAPTED FOR USE WITH OPERATING TABLES

[76] Inventor: Joseph T. McFadden, Treetops II-2D, 450 E. Lionshead Cir., P.O. Box 3039, Vail, Colo. 81658-39

[21] Appl. No.: 404,876

[22] Filed: Mar. 16, 1995

[51] Int. Cl.[6] .................................................. F16B 7/04
[52] U.S. Cl. .................. 403/53; 403/110; 403/181; 403/301; 403/321; 248/118; 5/637
[58] Field of Search .................. 403/55, 54, 53, 403/83, 84, 24, 110, 322, 324, 321, 62, 63, 300–302, 180–182; 248/118, 118.5, 118.1, 287.1, 278.1, 279.1; 5/621, 622, 658, 636, 637; 602/16–17; 606/54

[56] References Cited

U.S. PATENT DOCUMENTS

| | | | |
|---|---|---|---|
| 289,180 | 11/1883 | Tregurtha | 403/54 X |
| 3,188,079 | 6/1965 | Boetcker et al. | 5/622 |
| 4,108,426 | 8/1978 | Lindstroem et al. | 5/637 |
| 4,170,336 | 10/1979 | Malis | 248/279.1 |
| 4,392,645 | 7/1983 | Westphal | 5/637 |
| 4,964,748 | 10/1990 | McFadden | 403/55 |

FOREIGN PATENT DOCUMENTS

| | | | |
|---|---|---|---|
| 1445716 | 12/1988 | U.S.S.R. | 606/54 |

*Primary Examiner*—Kenneth J. Dorner
*Assistant Examiner*—Harry C. Kim
*Attorney, Agent, or Firm*—Cushman Darby & Cushman, L.L.P.

[57] ABSTRACT

A device for precisely positioning and locking an object in a selective position including a first arm, a second arm, a third arm and a fourth arm, as well as an L-shaped arm connecting the third and fourth arms. The arms are structured so as to movably connect a support for an object, such as a head rest, to a base member, such as an operating table. The arms are structured so as to slidably engage with one another in order to allow positioning of the support for the object in any desired position in a three dimensional space. The first arm is slidably mounted to a connection to the base member.

11 Claims, 2 Drawing Sheets

POSITIONING DEVICE ADAPTED FOR USE WITH OPERATING TABLES

BACKGROUND OF THE INVENTION

1. Field of the Invention

The present invention relates to a positioning device for an object, and, more specifically, to a device that will permit a user to position the object with one hand and to lock the positioning device in the desired orientation with his other hand, thus greatly facilitating the precise position of the object. The positioning device disclosed herein has particular utility in surgical procedures where the positioning of the patient's head with respect to an operating table is required.

2. Background Information

Generally, support devices for a portion of the anatomy of a patient that have been employed in medical procedures have emphasized stability and rigidity in their structure at the expense of ease of adjustment in view of the recognized importance of guarding against the desired movement of the patient during the medical procedure being carried out. Many prior art devices have the disadvantage that should one locking component of the positioning device be released accidentally during the surgical procedure, the head rest or positioning member could move, thus causing the patient to move undesirably.

U.S. Pat. No. 4,964,748 discloses a positioning device that may be used to position a patient's head during a surgical procedure. In this patent, if one of the clamping devices should accidentally be unlocked during a surgical procedure, there is a possibility that the patient's head could move, resulting in unwanted movement of the patient's entire body, which could disrupt the surgical procedure.

U.S. Pat. No. 4,157,876 discloses a lockable universally articulated joint in an orthopaedic appliance. A locking member is provided which includes a locking screw which extends through a socket and is threaded into a locking device. When the locking screw is loosened, the locking member allows universal articulation between the movable elements while preventing separation of these elements. Tightening of the screw effects clamping of the movable elements. This device does not provide the precise positioning nor any facility in repositioning the surgical site such as the head of a patient when used in conjunction with a head rest required in neurological surgery.

SUMMARY OF THE INVENTION

The present invention provides a positioning device which will allow a user to precisely position an object in a desired position quickly and efficiently. The present invention also provides a device to support the head of the patient during a surgical procedure with a built-in safety device that prevents failure to support the head. That is, the apparatus will not fail if a locking lever on the basic support mechanism is accidentally released during the surgical procedure.

In a preferred embodiment, the present invention comprises four arm members and an L-shaped arm member. The first and third arm members have opposite ends with locking members disposed thereon. The first end of the first arm is connected to a bracket for mounting to a base, such as an operating table. This first end is slidably engaged with a rod connected to the mounting member for the base. The first arm may be locked in any position along the rod. The second end of the first arm engages with a second arm that extends parallel to the rod of the connection of the base. A third arm extends from the second end of the second arm and is adjustably mounted on the second end of the second arm. The second end of the third arm includes a clamp connecting the third arm to the L-shaped arm. The L-shaped arm is slidably and lockably engaged with the fourth arm which extends to a connection device into which a positioning member, such as a clamp or head rest, is fitted. The positioning member fits into the fourth arm via a ball joint which allows positioning of the object to be operated upon in any desired position. By providing this combination of clamps connecting the various arms of the device together, unwanted movement of the patient's head or other bodily part being supported is avoided even if one of the locks is accidentally displaced during the surgical procedure.

BRIEF DESCRIPTION OF THE DRAWINGS

The above advantages and other advantages of the present invention along with the method of construction and the relationship between the parts of the apparatus will become apparent as consideration is given to the following detailed description taken in conjunction with the accompanying drawings in which.

DETAILED DESCRIPTION OF THE PRESENTLY PREFERRED EXEMPLARY EMBODIMENTS

Figure 1:
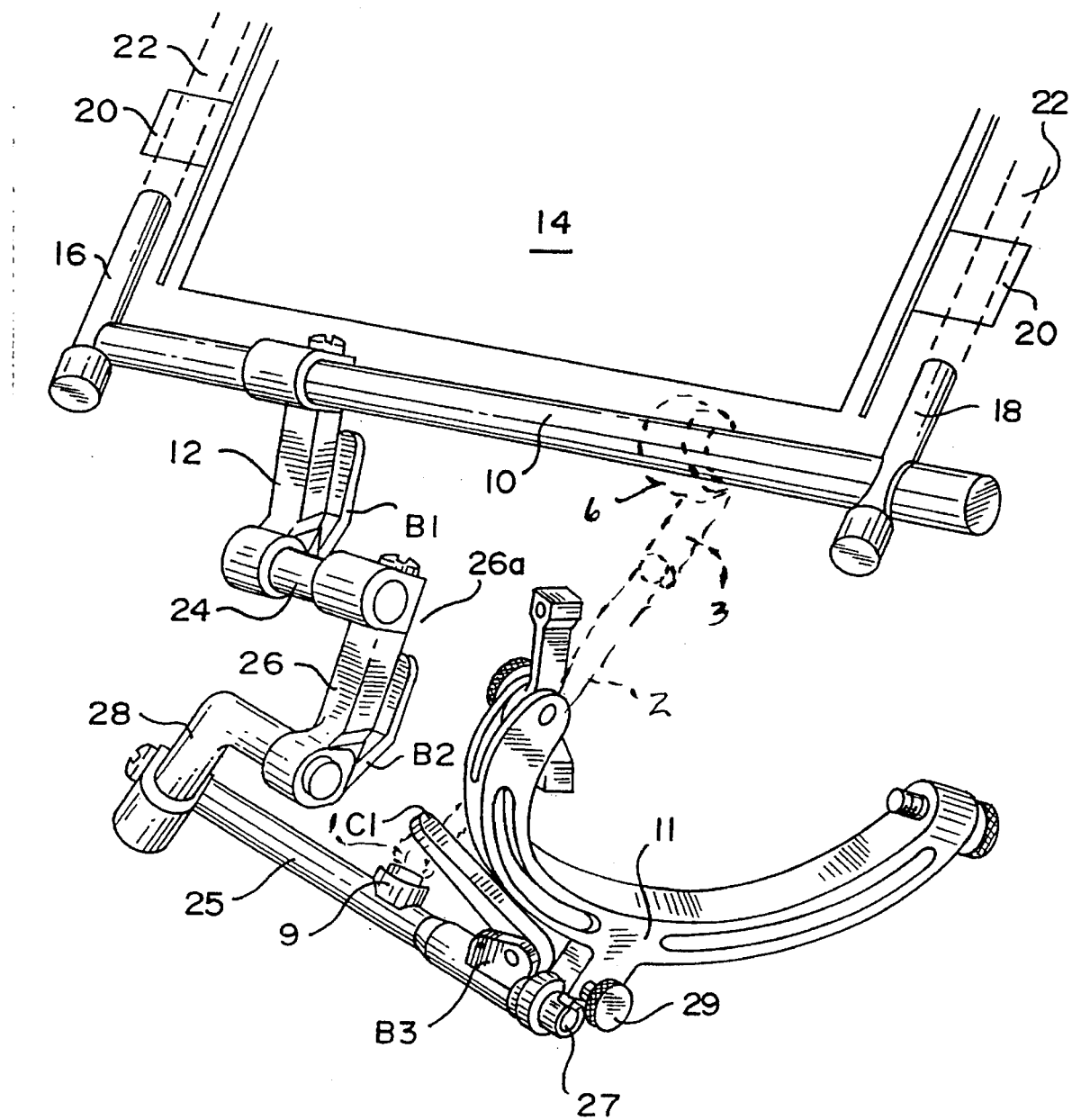
FIG. 1 is a perspective view showing the positioning device of the present invention mounted on a support shaft and bracket together with a head rest of the type used in neurological surgery.

A perspective view of the present invention is illustrated in FIG. 1.

First arm 12 attaches to horizontal rod 10 which in turn mounts to a base member 14 such as an operating table via rods 16 and 18. Each of rods 16 and 18 are disposed at a right angle to rod 10. Rods 16 and 18 slide into stirrup clamps 20 on side rails 22 of a base member 14, such as an operating table. Rod 16 is permanently fixed to rod 10 while rod 18 is slidably engaged with rod 10 via a hole formed in rod 18 so as to accommodate different size base members by allowing variation of the distance between rods 16 and 18. Stirrup clamps 20 include locking devices (not pictured) which lock the apparatus to the base member 14. Rods 16 and 18 include extensions (not pictured) that can be used to bring the rod 10 into a position above the patient in order to allow for another position, i.e. sitting, for the patient. Each of rods 16 and 18 includes a fastening mechanism (not pictured) that can secure them to stirrup clamps 20 in order to prevent the rods from falling therefrom.

First arm 12 is slidably disposed upon rod 10. That is, arm 12 may slide from rod 16 to rod 18 along rod 10. Arm 12 is secured to rod 10 via tightening of holding member 30 (see FIG. 3) which secures arm 12 to rod 10 at the position desired by the user. At a second end of arm 12, a clamp mechanism B1 is attached. Clamping mechanism B1 secures first arm 12 to second arm 24 as explained below. Arm 24 may be a simple, straight rod that extends between first arm 12 and third arm 26 or may be a right angle arm as is arm 28. The lever that operates clamping mechanism B1 faces the operating table 14.

Figure 3:
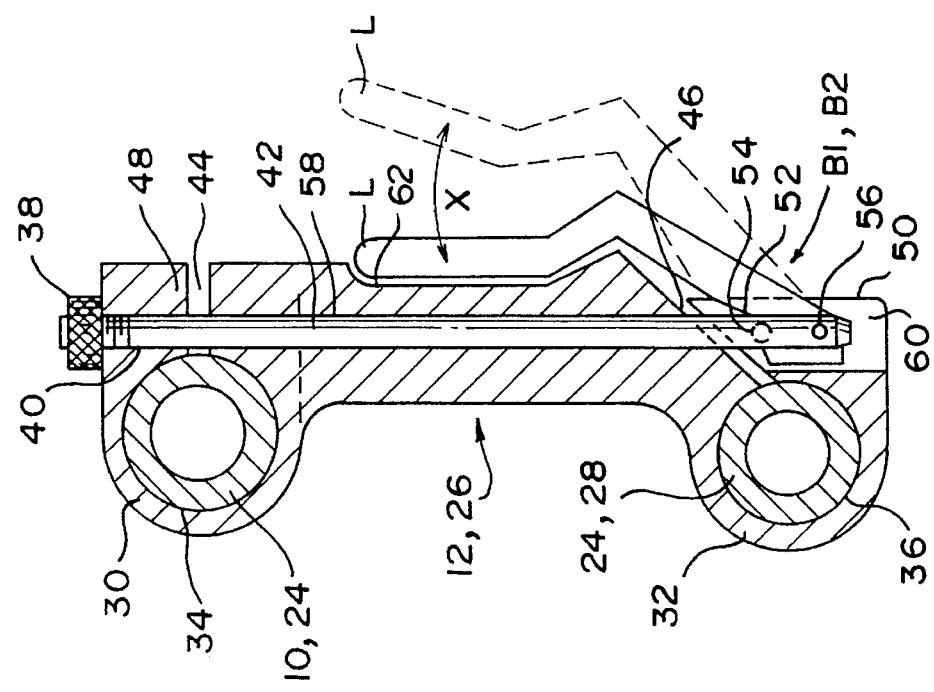
FIG. 3 depicts the first or third arms of the present invention and their relative orientations in a selected position.

FIG. 3 illustrates a detailed view of clamping mechanism B1 as used in first arm 12 or B2 as used in third arm 26. Both clamping mechanisms are the same in structure.

Arms 12 and 26 are identical in structure, so only a description of one arm is provided. Arms 12 and 26, depicted in FIG. 3, include clamping mechanisms B1, B2 respectively. The arms have a free leg 48 with a generally cylindrical recess 34 defined therein for closely interfitting engagement with the external shaft surface of arms 10, 24 or 28. Leg 48 is provided with a bore 40 for receiving a rod 42 which extends through bore 58 formed through the body of the arm 12, 26. Rod 42 extends to clamping mechanism B1, B2 located at the opposite end of arm members 12, 26. Bore 58 extends through leg 48 so that the rod 42 may extend through the leg 48 as illustrated. The exposed end of rod 42 is threaded to receive a threaded retaining ring 38. The opposite end of rod 42 is provided with a bore for receiving a retaining pin 56 which connects the end of the rod 42 to a locking lever L of each of the clamp mechanisms B1 and B2, as illustrated. On the inner side of its end adjacent to pin 56, locking lever L is provided with a camming surface 52. Recess 60 is provided on one wall thereof with a lug 54 that is positioned to engage the camming surface 52 of locking lever L. Camming surface 52 is shaped so that as lever L is moved between positions, with the range of movement being indicated by arrow X, lever L moves to its closed position indicated by the solid line or to an open position indicated by the dotted line. When lever L is in its closed and locked position, it secures in recess 62 formed in the main body of arm members 12, 26. When lever L is rotated clockwise, rod 42 will move to allow legs 48 and 50 to move away from the main body portion of the arm member 12, 26 to thereby open or release the circular holding members 30, 32, with holding member 30 holding rod 10 or 24 and holding member 32 securing arm 24 or 28. Holding members 30 and 32 are released or opened substantially at the same time. Rotation of the locking lever L in the counter clockwise direction into recess 62 will result in movement being transmitted to the legs 50 and 48 towards one another until the over-center position is reached on the camming surface 52 which, upon engagement with the lug 54 will effect locking of the lever L in the position within recess 62 and secure clamping of the holding members 30 and 32 about the associated elements 10, 24 or 24, 28 respectively. The degree of clamping force exerted can be varied by loosening or tightening the threaded ring 38 on the threaded end of rod 42.

Gaps 44 and 46 in the holding members 30 and 32, respectively, are dimensioned to provide the required amount of play in legs 48 and 50, respectively.

Third arm 26 is secured to second arm 24 via holding member 30 (FIG. 3). This allows the first end 26a of third arm 26 to be slidable and rotatable on second arm 24. The third arm 26 is identical in structure to the first arm 12. Thus, third arm 26 includes clamping mechanism B2 at a second end thereof with clamping mechanism B2 being the same as B1. Clamping mechanism B2 couples third arm 26 to L-shaped arm 28 in holding member 32 (FIG. 3). Arm 28 is slidably engaged to fourth arm 25 via a cylindrical bore 36 which includes a clamping mechanism B3 similar to that of the clamping mechanisms B1 and B2 found in first and third arms 12 and 26, respectively. Thus, description thereof is omitted. At a second end of fourth arm 25, a ball socket 27 is disposed. Ball socket 27 is tightened by clamping arm C1 of clamping mechanism B3.

Each of the arms which secures clamping mechanism B1 and clamping mechanism B2 is shorter than the length of the first arm 12 or third arm 26, respectively. The distal end of each lever locks into the closed position with a detent or similar snap lock to prevent accidental opening with single hand motion. That is, the opening of the lever requires two separate and deliberate acts in order to (1) unlock the lever and (2) then unlock the joint. Each of the levers of clamping mechanism B1 that secures arm 12, clamping mechanism B2 that secures arm 26, and clamping mechanism B3 that secures arm 25, has a short opening range that prevents throwing the levers into a position which would interfere with motion of the assembled apparatus.

Head clamp 11 snaps to the stem of ball-socket 27 by a detent or a similar mechanism and is then secured with a second locking device 29 for security. A head rest (not shown) may be attached instead of the head clamp 11 for comfortably supporting the head of a patient. The clamp or head supporting mechanism comes in a variety of sizes and can be made from a variety of materials for specific purposes. The size of the head clamp varies according to head size of the patient and according to the reach needed for a particular operative approach: i.e., interior-posterior reach, oblique reach, or side to side reach on the cranium. The material of the head clamp varies with the operative needs. For intraoperative diagnostic procedures such as angiography, MRI, or cat scans, non-metallic, radiolucent, non-ferromagnetic materials are used. For intraoperative targeting, the same type of materials may be used. For other types of operations, a metallic head clamp is normally used.

The first, third and fourth arms are approximately five inches long, thus creating a possible, approximate total length of 15 inches from rod 10 to ball socket 27. Of course, variations in size are possible for different applications.

In a second embodiment of the present invention (not pictured), the L-shaped arm 28 could replace the second arm 24, thereby giving the assembled apparatus a different range of motion. That is, L-shaped arm 28 could be used to attach first arm 12 directly to fourth arm 25, thus eliminating third arm 26, in order to set up a two joint apparatus having a different range of motion.

Figure 2:
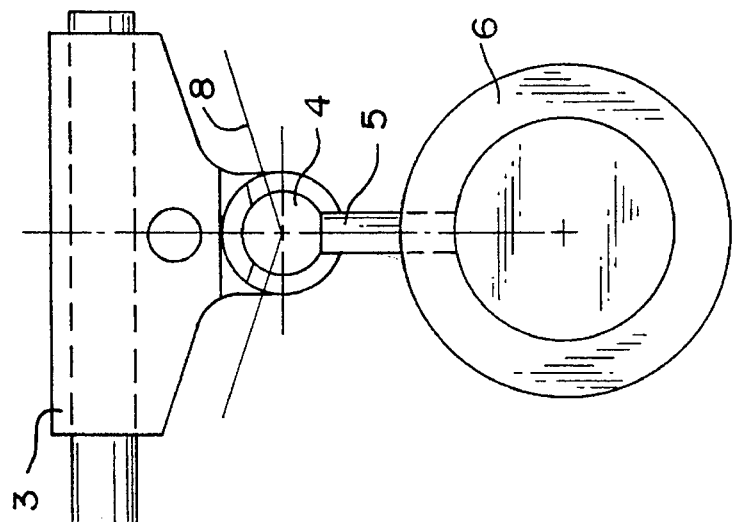
FIG. 2 illustrates a safety mechanism for attaching the present invention to a base member such as an operating table.

FIG. 2 illustrates a cross sectional view of a safety device that secures the present invention in the position desired by the user. The safety device includes a ball 1 which fits into ball socket 9 (FIG. 1) disposed toward the distal end of fourth arm 25 in a position below the clamping arm C1. In FIG. 1, the positioning of the safety device 2 is shown in dotted lines with the ring 6 and ball 1 in position between the rod 10 and the arm 25. Ball 1 is securely fastened to rod 2 which in turn is slidably disposed within housing 3. Ring 6 is attached to housing 3 via a stem 5 and a ball mechanism 4. Ball 4 fits in housing 3. Ring 6 is fitted around rod 10. Clamp 8 disposed on housing 3 secures the ball 4 in a desired position so as to prevent movement of stem 5 and ring 6. When clamp 8 is secured, it is no longer possible to move ring 6 along rod 10. When the entire mechanism shown in FIG. 1 is adjusted to its desired position, ball 1 rocks in socket 9, rod 2 slides in housing 3, housing 3 rocks on ball 4, and ring 6 rocks and slides along rod 10. Clamp 8 secures ball 4, thus securing the position of the safety device after the apparatus is adjusted to the desired position.

With the structure of this invention, the support will have a three dimensional range of adjustment which has previously has been unavailable to the practitioner.

The present invention has been described in connection with what is presently considered to be the preferred embodiment of the present invention. However, various modifications are possible, and are intended to be included within the spirit and scope of the appended claims.

What is claimed is:

1. A device in combination with an object and a base for positioning said object relative to said base comprising:

first, second, third, and fourth arms, an L-shaped arm connecting said third arm and said fourth arm, said first and third arms having first and second opposite ends, each said end of said respective first and third arms having holding members movable between a locked position and unlocked position, said first and third arms each further including movable actuating means for substantially simultaneously moving each of said holding members of said respective first and third arms between said locked and unlocked positions in response to movement of said respective actuating means between an actuated position and a deactuated position, a first connecting means releasably and rotatably engaged with said second arm by said holding member of said second end of said first arm, said first connecting means being slidable with respect to said second arm, a second connecting means releasably and rotatably engaged with said second arm at an end thereof opposite said first arm by said holding member of said first end of said third arm, said third arm being slidable with respect to said second arm, a third connecting means releasably and rotatably engaged with a first end of said L-shaped arm by said holding member at said second end of said third arm, a fourth connecting means releasably and rotatably engaged with a second end of said L-shaped arm by a clamp disposed at a first end of said fourth arm, said fourth arm including a connection to a positioning member adjacent a second end of said fourth arm, said connection being able to lock said positioning member in a desired position.

2. A device in combination with an object and a base as claimed in claim 1, wherein the base is of the type having a support rod and said holding member at said first end of said first arm is provided for connection of said device to the support rod.

3. A device in combination with an object and a base as claimed in claim 2, wherein said base is an operating table.

4. A device in combination with an object and a base as claimed in claim 3, wherein said positioning member is a headrest.

5. A device in combination with an object and a base as claimed in claim 2, wherein said first arm is slidable with respect to said support rod.

6. A device in combination with an object and a base as claimed in claim 2, further comprising a safety mechanism extending between the support rod and said fourth arm.

7. A device in combination with an object and a base as claimed in claim 6, wherein said safety mechanism is connected to said fourth arm via a ball joint disposed proximate the distal end thereof.

8. A device in combination with an object and a base as claimed in claim 7, wherein said ball joint includes a ball disposed therein and said ball joint allows the ball disposed therein to rotate freely, thus allowing positioning of said device.

9. A device in combination with an object and a base as claimed in claim 6, wherein said support rod includes a first rod slidably disposed perpendicular to said first arm, a second rod permanently connected to said base, and a third rod which is slidable with respect to said first rod, said second and third rods being adapted to attach to the base.

10. A device in combination with an object and a base as claimed in claim 9, wherein said safety mechanism includes a second end through which said first rod is slidably disposed.

11. A device in combination with an object and a base as claimed in claim 1, wherein said connection to said positioning member at said second end of said fourth arm is a ball joint allowing easy positioning of said positioning member.

\* \* \* \* \*